(12) United States Patent
Okamoto et al.

(10) Patent No.: US 7,193,118 B2
(45) Date of Patent: Mar. 20, 2007

(54) METHOD FOR PRODUCING FLUOROALKYL ETHER

(75) Inventors: Hidekazu Okamoto, Yokohama (JP); Masazumi Nagai, Ichihara (JP); Kazuya Oharu, Yokohama (JP)

(73) Assignee: Asahi Glass Company, Limited, Tokyo (JP)

( * ) Notice: Subject to any disclaimer, the term of this patent is extended or adjusted under 35 U.S.C. 154(b) by 0 days.

(21) Appl. No.: 11/293,200

(22) Filed: Dec. 5, 2005

(65) Prior Publication Data

US 2006/0094908 A1    May 4, 2006

Related U.S. Application Data

(63) Continuation of application No. PCT/JP04/008075, filed on Jun. 3, 2004.

(30) Foreign Application Priority Data

Jun. 4, 2003    (JP) .............................. 2003-159342

(51) Int. Cl.
*C07C 41/06*    (2006.01)
(52) U.S. Cl. ....................... 568/683; 568/684; 568/697
(58) Field of Classification Search ................ 568/683, 568/684, 697
See application file for complete search history.

(56) References Cited

U.S. PATENT DOCUMENTS 2,973,389 A * 2/1961 Weissermel et al. ........ 568/677
3,557,294 A   1/1971 Dear et al. ................... 514/722
3,764,706 A   10/1973 Terrell ......................... 424/342

FOREIGN PATENT DOCUMENTS

JP    9-263559     10/1997
JP    2002-201152  7/2002

OTHER PUBLICATIONS

Machine translation of JP 09-263559 A.*
R. E. A. Dear, et al., "Polyhaloethers from the Reaction of Fluoroalcohols and Haloolefins", Journal of Chemical Engineering Data, vol. 14, No. 4, XP-002396631, Oct. 1969, pp. 493-497.
Junji Murata, et al., "Selective synthesis of fluorinated ethers by addition reaction of alcohols to fluorinated olefins in water", Green Chemistry, vol. 4, No. 1, XP-008067976, 2002, pp. 60-63.
Albert L. Henne, et al., "Fluorinated Ethers", Journal of the American Chemical Society, vol. 72, XP-002396632, 1950, pp. 4378-4380.

* cited by examiner

*Primary Examiner*—Rosalynd Keys
(74) *Attorney, Agent, or Firm*—Oblon, Spivak, McClelland, Maier & Neustadt, P.C.

(57) ABSTRACT

A method for producing a fluoroalkyl ether, which comprises reacting a fluoroalkyl alcohol with a fluorinated olefin in the presence of a solvent and a catalyst, wherein the fluoroalkyl alcohol and the fluorinated olefin are continuously supplied into a reactor, a reaction product containing the fluoroalkyl ether is continuously withdrawn from the reactor, and the reaction is carried out while the concentration of the fluoroalkyl alcohol present in the reactor is maintained to be at most 7 mass % based on the total organic component present in the reactor. According to the present invention, a fluoroalkyl ether having a high purity can be produced in an industrial scale and at a high reaction rate.

20 Claims, 2 Drawing Sheets

METHOD FOR PRODUCING FLUOROALKYL ETHER

TECHNICAL FIELD

The present invention relates to a technique for producing an industrially useful fluoroalkyl ether (hereinafter referred to as HFE) simply and in good yield.

BACKGROUND ART

A fluoroalkyl ether is a compound which has attracted attention in recent years as a substitute for a chlorofluorocarbon which used to be employed as freon. It has a short life in the atmosphere and has no chlorine atom, and it thus is characterized in that it presents little adverse effect to the global environment such as ozone depletion or global warming.

With respect to a method for preparing a fluoroalkyl ether, various methods have been reported. As a method for the preparation in an industrial scale, an addition reaction of a fluoroalkyl alcohol with a fluorinated olefin in the presence of an alkali, is known (U.S. Pat. No. 3,557,294). However, this reaction requires a relatively high temperature and a high reaction pressure, and the reaction rate is extremely low.

As a method to improve over such problems, a method of reacting a fluoroalkyl alcohol with a fluorinated olefin in a solvent, has been reported (claims and Examples in JP-A-9-263559). However, also in this method, the reaction rate is not adequate, and particularly in a batch system reaction as disclosed in the Examples, the rate in the initial stage of the reaction is very low, and there has been a problem that no adequate efficiency can be obtained for the practical production.

It is an object of the present invention to provide an efficient method for producing a fluoroalkyl ether, whereby the reaction rate is high, and the production in an industrial scale is possible.

DISCLOSURE OF THE INVENTION

The present invention provides a method for producing a fluoroalkyl ether, which comprises reacting a fluoroalkyl alcohol with a fluorinated olefin in the presence of a solvent and a catalyst, wherein the fluoroalkyl alcohol and the fluorinated olefin are continuously supplied into a reactor, a reaction product containing the fluoroalkyl ether is continuously withdrawn from the reactor, and the reaction is carried out while the concentration of the fluoroalkyl alcohol present in the reactor is maintained to be at most 7 mass % based on the total organic component present in the reactor.

The present inventors have studied the change with time of the reaction rate in a batch reaction in detail, and have surprisingly found that the reaction rate abruptly increases at the end stage of the reaction i.e. the stage at which the residual concentration of the fluoroalkyl alcohol used as the starting material has decreased to not more than a certain concentration, and particularly at the terminal stage of the reaction where the concentration of the fluoroalkyl alcohol decreases to not higher than 7% (based on mass), it is remarkably accelerated. This is considered attributable to the fact that as the concentration of the fluoroalkyl alcohol decreases, the solubility of the fluorinated olefin increases.

On this basis, it has been found possible to remarkably improve the productivity by a method of maintaining the composition corresponding to the terminal stage of the reaction in the batch reaction, from the beginning of the reaction, i.e. the method wherein the reaction is carried out in a continuous reaction system wherein the fluoroalkyl alcohol and the fluorinated olefin as raw materials are continuously supplied into an organic phase containing the fluoroalkyl ether as the reaction product and the solvent, and the formed reaction crude liquid is continuously withdrawn, and the concentration of the fluoroalkyl alcohol in the organic component present in the reaction system is maintained to be at most 7 mass %, and the present invention has been accomplished on the basis of this discovery.

MEANING OF SYMBOLS

RE: reactor, VE: vessel, CD: condenser

BEST MODE FOR CARRYING OUT THE INVENTION

Figure 1:
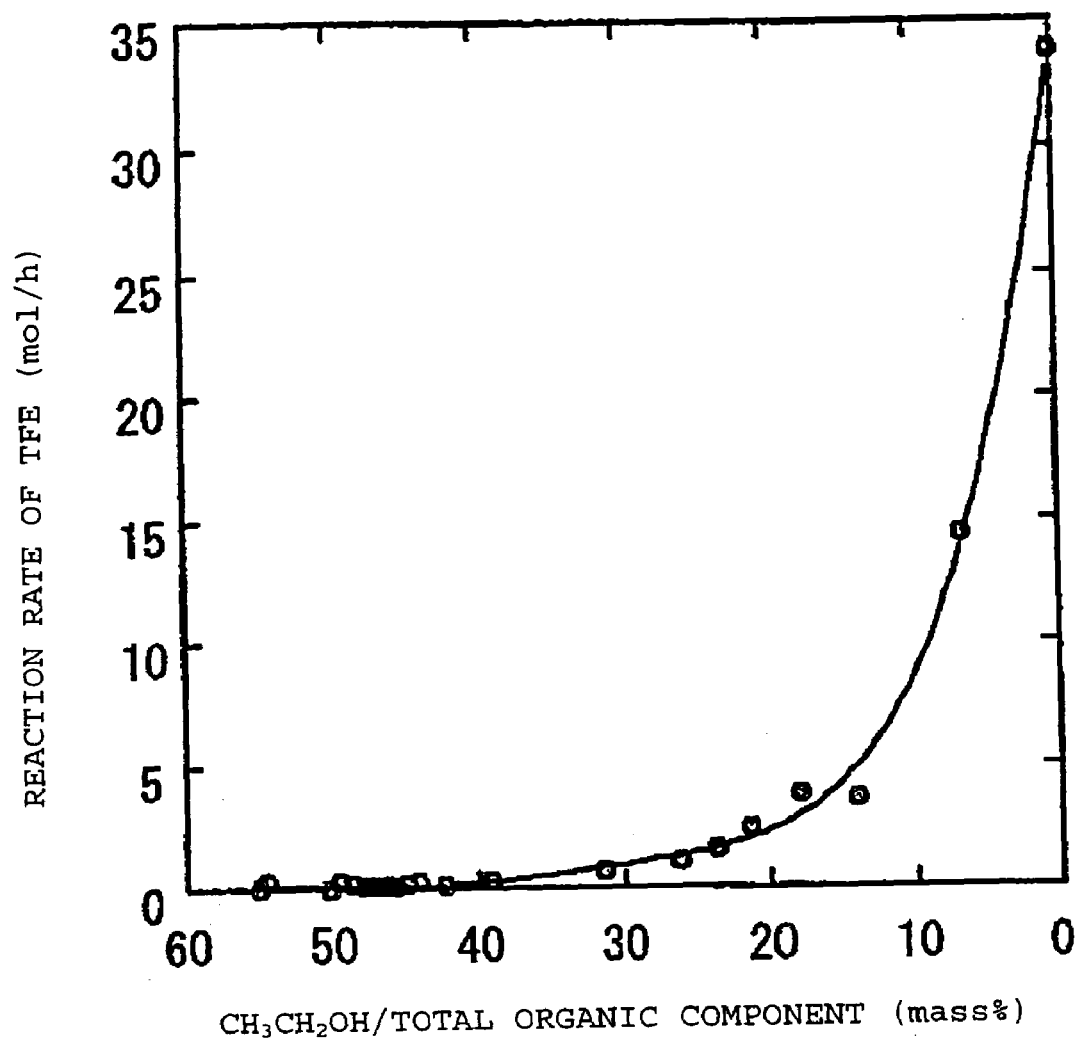
FIG. 1 is a correlation diagram between the $CF_3CH_2OH$-remaining amount and the reaction rate.

In the present invention, the concentration of the fluoroalkyl alcohol present in the reactor is at most 7 mass % based on the total organic component present in the reactor. However, from the viewpoint of the efficiency at the time of distillation or purification after completion of the reaction, the concentration is preferably at most 3 mass %, more preferably at most 1 mass %.

The raw material fluoroalkyl alcohol to be used in the present invention may be any alcohol so long as it is a compound having hydrogen of other than the hydroxyl group of a hydrocarbon alcohol partially substituted by fluorine atoms, and it may be an alcohol having a fluorocycloalkyl group. However, it is preferably a compound represented by the formula 1 when the production in an industrial scale of the fluoroalkyl ether as the product and the effects in the applied field are taken into consideration.

  Formula 1 wherein Rf is $-C_aH_bF_dX_e$, where X is a halogen atom other than a fluorine atom, each of a and d which are independent of each other, is an integer of at least 1, each of b and e which are independent of each other, is an integer of at least 0, and $b+d+e=2a+1$.

From the viewpoint of the availability, a in the formula 1 is preferably an integer of from 1 to 10, particularly preferably an integer of from 2 to 4. Further, e is preferably 0.

Among compounds represented by the formula 1, fluoroalkyl alcohols to be preferably employed, may specifically be $CF_3CH_2OH$, $CF_3CF_2CH_2OH$, $CF_3(CF_2)_2CH_2OH$, $CF_3(CF_2)_3CH_2OH$, $CF_3(CF_2)_4CH_2OH$, $CF_3(CF_2)_5CH_2OH$, $CF_3(CF_2)_6CH_2OH$, $CHF_2CF_2CH_2OH$, $CHF_2(CF_2)_3CH_2OH$, $CHF_2(CF_2)_5CH_2OH$, $CF_3CHFCF_2CH_2OH$ and $CHF_2CF(CF_3)CH_2OH$. Among them, a fluoroalkyl alcohol to be particularly preferably used, may be 2,2,2-trifluoroethanol ($CF_3CH_2OH$, hereinafter referred to as TFEO).

Further, as the fluorinated olefin as another raw material in the present invention, a compound represented by the formula 2 is preferred.

  Formula 2 wherein each of Y and Z which are independent of each other, is a hydrogen atom, a fluorine atom or a trifluoromethyl group.

The compound represented by the formula 2 may specifically be $CF_2=CF_2$, $CF_2=CHF$, $CF_2=CH_2$ or $CF_2=CFCF_3$. Among them, a perfluoroolefin is preferred, and most preferably employed is tetrafluoroethylene ($CF_2=CF_2$, hereinafter referred to as TFE).

Further, it is preferred to apply the method of the present invention to a case where 1,1,2,2-tetrafluoro-1-(2,2,2-trifluoroethoxy)ethane is produced as the fluoroalkyl ether by using 2,2,2-trifluoroethanol (TFEO) as the fluoroalkyl alcohol and tetrafluoroethylene (TFE) as the fluorinated olefin.

Further, it is preferred to apply the method of the present invention to a method for producing 1,1,2,3,3,3-hexafluoro-1-(2,2,3,3-tetrafluoropropoxy)propane by using 2,2,3,3-tetrafluoro-1-propanol and hexafluoropropene, or a method for producing 1,1,2,3,3,3-hexafluoro-1-(2,2,2-trifluoroethoxy)propane by using 2,2,2-trifluoroethanol and hexafluoropropene.

The catalyst to be used in the present invention is not particularly limited so long as it is a basic compound. However, from the viewpoint of the intensity of the basicity and general applicability, it is preferred to employ an alkali metal alkoxide or an alkali metal hydroxide.

As the alkali metal alkoxide, a commercial product may be used as it is, but one obtained by reacting an alkali metal, an alkali metal hydride or an alkali metal amide with an alcohol, may be employed. The alcohol to be used for this reaction is not particularly limited, but it is preferred to employ the fluoroalkyl alcohol to be used as the raw material in the present invention. Further, in the above reaction, the alkali metal may, for example, be Na, K or Cs, the alkali metal hydride may, for example, be NaH or KH, and the alkali metal amide may, for example, be $NaNH_2$ or $KNH_2$.

Further, as the alkali metal hydroxide, NaOH or KOH may, for example, be used particularly preferably from the viewpoint of handling efficiency and general applicability. Such an alkali metal hydroxide has a merit that it can be used in the form of an aqueous solution. In a case where the reaction is carried out continuously as in the present invention, it is also necessary to continuously supply the catalyst. In such a case, it is preferred to supply the catalyst in the form of a solution. Accordingly, in the present invention, it is particularly preferred to use an aqueous solution of an alkali metal hydroxide as the catalyst.

In the present invention, the concentration of the catalyst is not particularly limited, but from the viewpoint of the reaction rate and economical efficiency, it is preferably from 0.005 to 1 mol equivalent to the fluoroalkyl alcohol as the raw material, and particularly preferably, it is from 0.05 to 0.5 mol equivalent to obtain an economical reaction rate.

In the present invention, it is possible to improve the reaction rate by employing a solvent. As such a solvent, an aprotic polar solvent is preferred, and a straight chain ether such as diethyl ether or a glyme, a cyclic ether such as dioxane or tetrahydrofuran, or a nitrile compound such as acetonitrile or propionitrile, may be mentioned. Among them, a glyme such as tetraglyme is particularly preferably employed, since it is possible to further improve the reaction rate and it can easily be separated from the reaction product.

The content of the solvent in the reactor is preferably from 0.01/1 to 0.8/1, more preferably from 0.05/1 to 0.5/1, by mass ratio to the total amount of the fluoroalkyl ether and the solvent.

In the present invention, in order to maintain the concentration of the fluoroalkyl alcohol present in the reactor to be at most 7 mass % based on the total organic component present in the reactor, a so-called continuous reaction process is employed wherein the fluoroalkyl alcohol and the fluorinated olefin are continuously supplied to the reactor together with the solvent and the catalyst, and the reaction product containing the fluoroalkyl ether is continuously withdrawn from the reactor. This continuous reaction process is a method whereby production in an industrial scale is possible.

In this continuous process, in order to maintain the concentration of the fluoroalkyl alcohol present in the reactor to be always at most 7 mass % based on the total organic component present in the reactor, it is necessary to balance the amount of the fluoroalkyl alcohol to be consumed by the reaction and the amount of the fluoroalkyl alcohol to be continuously supplied into the reactor.

For this purpose, it is preferred to supply the fluorinated olefin always in excess to the fluoroalkyl alcohol to be supplied as the raw material, and it is preferred to supply the respective materials continuously so that the supplying molar ratio of the fluorinated olefin to the fluoroalkyl alcohol (the fluorinated olefin/the fluoroalkyl alcohol) would be at least 1, particularly preferably at least 1.05.

Further, in many cases, the fluoroalkyl alcohol to be used in the present invention has a boiling point close to the boiling point of the fluoroalkyl ether as the desired product, and in a case where the concentration of the fluoroalkyl alcohol remaining in the reaction crude liquid is high, there is a problem such that it becomes difficult to separate the fluoroalkyl alcohol and the fluoroalkyl ether by distillation as a common purification method.

This problem is very important in a case where 1,1,2,2-tetrafluoro-1-(2,2,2-trifluoroethoxy)ethane (hereinafter referred to as HFE-347 pc-f) is produced as the fluoroalkyl ether by using TFEO as the fluoroalkyl alcohol and TFE as the fluorinated olefin. Namely, TFEO and HFE-347 pc-f will constitute an azeotropic composition, whereby it is difficult to obtain HFE-347 pc-f of high purity by distillation.

Therefore, in the method for producing such HFE-347 pc-f, the reaction is carried out by adjusting the concentration of TFEO present in the reactor to be at most 7 mass %, preferably at most 3 mass %, more preferably at most 1 mass %, particularly preferably at most 0.5 mass %, based on the total organic component including HFE-347 pc-f present in the reactor.

In the present invention, the reaction temperature may vary depending upon the types of the fluoroalkyl alcohol, the fluorinated olefin and the catalyst, etc., but it is usually preferably within a range of from room temperature to 120° C., particularly preferably from 30 to 80° C.

In the present invention, the reaction pressure may vary depending upon the fluorinated olefin and the reaction temperature. However, if the reaction is carried out under a pressure being too high, the possibility for polymerization of the fluoroolefin or a danger such as explosion will increase. Accordingly, the pressure is preferably within a range of from the atmospheric pressure to 2 MPa (gauge pressure), particularly preferably from 0.01 to 1 MPa (gauge pressure).

In this reaction, in a case where relatively high reaction temperature or pressure condition is employed, the fluorinated olefin is likely to undergo a polymerization reaction. In such a case, it is preferred to add a polymerization inhibitor for the purpose of preventing such polymerization. The polymerization inhibitor may be introduced continuously into the reactor together with the raw materials or the solvent. The polymerization inhibitor is not particularly limited so long as it is a compound capable of substantially preventing the polymerization of the fluorinated olefin, and limonene, pinene, cymeme or terpinene may, for example, be mentioned.

EXAMPLES

Now, the present invention will be described with reference to Examples (Examples 1 and 2) and Comparative Example (Example 3).

Example 1

Into a pressure resistant reactor having an internal capacity of 1 L, 300 g of 2,2,2-trifluoroethanol (TFEO), 200 g of acetonitrile and 20 g of a 48 mass % KOH aqueous solution were charged, and then, oxygen in the reactor was removed by vacuum deaeration. The reactor was set in a warm water bath so that the internal temperature of the reactor would be 60° C., and tetrafluoroethylene (TFE) was continuously supplied into the reactor so that the internal pressure of the reactor would be constant at 0.5 MPa. The amount of TFE supplied and the result of the analysis of the liquid composition in the reactor by gas chromatograph, were analyzed to obtain the correlation between the composition (mass %) of TFEO based on the total organic component in the reactor and the consumption molar rate of TFE per unit hour. The results are shown in FIG. 1.

Example 2

Now, a synthetic test of HFE-347 pc-f will be described.

Figure 2:
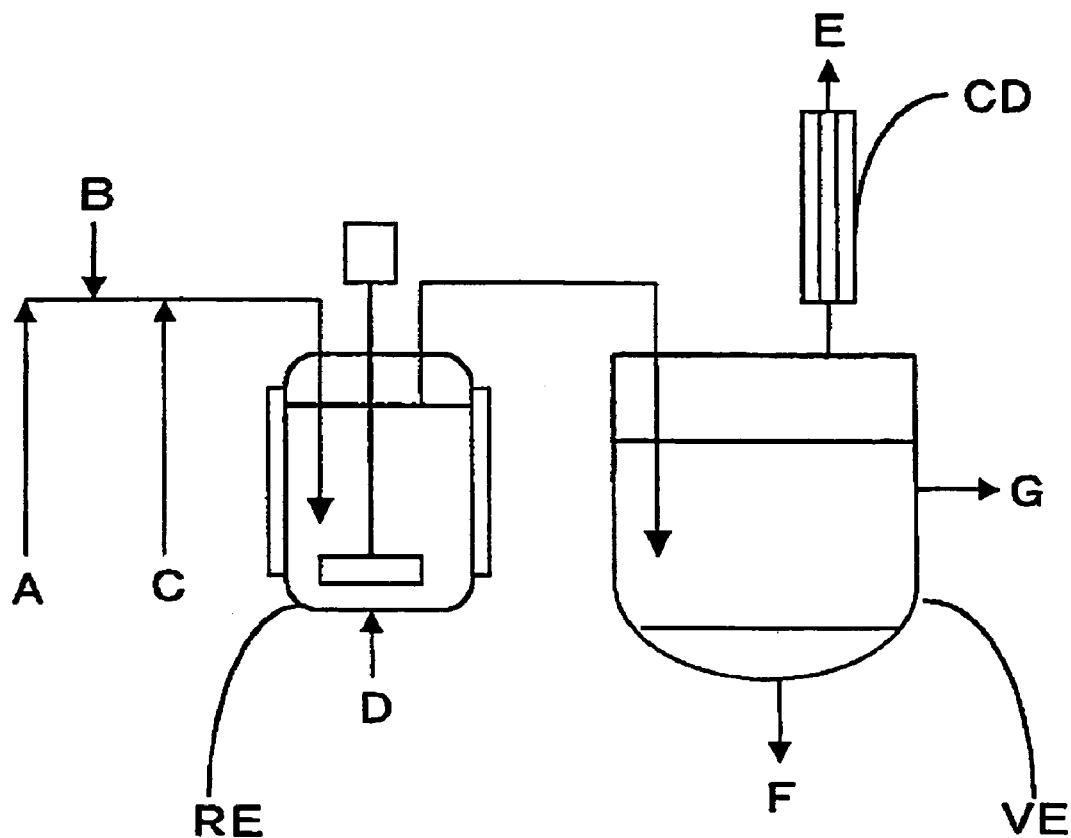
FIG. 2 is a view illustrating a reaction apparatus to be used for carrying out the present invention.

In FIG. 2, RE represents a reactor having an internal capacity of 300 L, VE represents a vessel serving also as a liquid-liquid separation tank having an internal capacity of 1,000 L, and CD represents a condenser capable of cooling brine. Using this reaction apparatus, a synthetic reaction was carried out by the following method.

Into the reactor RE, 277 kg of HFE-347 pc-f, 42 kg of tetraglyme and 32 kg of a 48 mass % potassium hydroxide aqueous solution were charged, and then, the temperature was raised to 60° C. A reaction was carried out by continuously supplying 43 kg/hr of TFE from A, 41 kg/hr of TFEO from B, 12 kg/hr of tetraglyme from C and 8.4 kg/hr of the 48 mass % potassium hydroxide aqueous solution from D with stirring, so that the pressure in the reactor was maintained to be 0.15 MPa, and the temperature was maintained at 60° C.

A continuous operation was carried out by permitting HFE-347 pc-f formed by the reaction to overflow from the top of the reactor RE to the vessel VE side together with tetraglyme and the potassium hydroxide aqueous solution. The gas component containing unreacted TFE was purged to the outside via the condenser CD cooled to 0° C.

For the reaction results, a part of the reaction crude liquid overflown from the reactor RE was sampled from time to time, and the organic phase was analyzed by gas chromatograph. The composition of the reaction crude liquid analyzed every two hours is shown in Table 1. Here, the main component of "Other" in Table 1 is TFE dissolved in the liquid.

The reaction was continued for 10 hours, and 1,000 kg of the reaction crude liquid including the aqueous phase in the vessel VE was recovered. The organic component therein was 915 kg. The composition of the recovered organic component was analyzed by gas chromatograph, and the results are also shown in Table 1.

TABLE 1

| Lapsed time (hr) | CF$_3$CH$_2$OH (mass %) | HFE-347pc-f (mass %) | Tetraglyme (mass %) | Others (mass %) |
| --- | --- | --- | --- | --- |
| 2 | 0.12 | 85.7 | 11.5 | 2.6 |
| 4 | 0.08 | 84.2 | 12.2 | 3.5 |
| 6 | 0.005 | 84.4 | 12.1 | 3.4 |
| 8 | 0.025 | 85.1 | 11.9 | 2.9 |
| 10 | 0.085 | 84.5 | 12.3 | 3.1 |
| Crude liquid in vessel VE | 0.08 | 84.6 | 12.1 | 3.2 |

915 kg of the organic crude liquid recovered in the vessel VE was charged into a distillation column having a bottom capacity of 1 m$^3$ and a theoretical plate number of 20 plates. Then, the bottom was heated and refluxed. After the operation for one hour under total reflux, distillation was carried out at a reflux ratio of 1. A fraction having a purity of HFE-347 pc-f being at least 99.8 mol %, was recovered to obtain 730 kg of the product. The distillation yield was 94%.

Example 3 (Comparative Example)

Using the reaction apparatus shown in FIG. 2 in the same manner as in Example 2, a synthetic reaction was carried out as follows.

Into the reactor RE, 242 kg of HFE-347 pc-f, 35 kg of TFEO, 42 kg of tetraglyme and 32 kg of a 48 mass % potassium hydroxide aqueous solution were charged, and then, the temperature was raised to 60° C. A reaction was carried out by continuously supplying 43 kg/hr of TFE from A, 41 kg/hr of TFEO from B, 12 kg/hr of tetraglyme from C and 8.4 kg/hr of the 48 mass % potassium hydroxide aqueous solution from D with stirring, so that the pressure in the reactor was maintained to be 0.15 MPa, and the temperature was maintained at 60° C.

A continuous operation was carried out by permitting HFE-347 pc-f formed by the reaction to overflow from the top of the reactor RE to the vessel VE side together with tetraglyme and the potassium hydroxide aqueous solution. The gas component including unreacted TFE was purged to the outside via the condenser CD cooled to 0° C.

For the reaction results, a part of the reaction crude liquid overflown from the reactor RE was sampled from time to time, and the organic phase was analyzed by gas chromatograph. The composition of the reaction crude liquid sampled and analyzed every two hours, is shown in Table 2.

The reaction was continued for 10 hours, and 940 kg of the reaction crude liquid including the aqueous phase was recovered in the vessel VE. The organic component therein was 855 kg. The composition of the recovered organic component was analyzed by gas chromatograph, and the results are also shown in Table 2.

TABLE 2

| Lapsed time (hr) | CF$_3$CH$_2$OH (mass %) | HFE-347pc-f (mass %) | Tetraglyme (mass %) | Other (mass %) |
| --- | --- | --- | --- | --- |
| 2 | 12.5 | 72.4 | 11.5 | 3.6 |
| 4 | 14.9 | 66.8 | 12.8 | 5.5 |
| 6 | 18.5 | 62.5 | 13.6 | 5.4 |
| 8 | 24.1 | 55.7 | 14.3 | 5.9 |
| 10 | 33.9 | 45.0 | 15.0 | 6.1 |
| Crude liquid in vessel VE | 20.5 | 60.5 | 13.5 | 5.5 |

845 kg of the organic crude liquid recovered in the vessel VE was subjected to distillation by using the same distillation column as in Example 2 under the same operational conditions. However, no fraction of HFE-347 pc-f having a purity of at least 99.8 mol %, was recovered at all.

INDUSTRIAL APPLICABILITY

According to the present invention, it is possible to produce a fluoroalkyl ether of high purity in an industrial scale and at a high reaction rate. Further, according to the present invention, a post-step such as distillation after the reaction can be carried out efficiently.

The entire disclosure of Japanese Patent Application No. 2003-159342 filed on Jun. 4, 2003 including specification, claims, drawings and summary is incorporated herein by reference in its entirety.

What is claimed is:

1. A method for producing a fluoroalkyl ether, which comprises reacting a fluoroalkyl alcohol with a fluorinated olefin in the presence of a solvent and a catalyst, wherein the fluoroalkyl alcohol and the fluorinated olefin are continuously supplied into a reactor, a reaction product containing the fluoroalkyl ether is continuously withdrawn from the reactor, and the reaction is carried out while the concentration of the fluoroalkyl alcohol present in the reactor is maintained to be at most 7 mass % based on the total organic component present in the reactor.

2. The method for producing a fluoroalkyl ether according to claim 1, wherein the fluoroalkyl alcohol is a compound represented by the formula 1:

RfCH$_2$OH　　　　Formula 1 wherein Rf is —C$_a$H$_b$F$_d$X$_e$, where X is a halogen atom other than a fluorine atom, each of a and d which are independent of each other, is an integer of at least 1, each of b and e which are independent of each other, is an integer of at least 0, and b+d+e=2a+1.

3. The method for producing a fluoroalkyl ether according to claim 1, wherein the fluorinated olefin is a compound represented by the formula 2:

CF$_2$=CYZ　　　　Formula 2 wherein each of Y and Z which are independent of each other, is a hydrogen atom, a fluorine atom or a trifluoromethyl group.

4. The method according to claim 1 for producing 1,1,2,2-tetrafluoro-1-(2,2,2-trifluoroethoxy)ethane as the fluoroalkyl ether, wherein the fluoroalkyl alcohol is 2,2,2-trifluoroethanol (hereinafter referred to as TFEO), and the fluorinated olefin is tetrafluoroethylene (hereinafter referred to as TFE).

5. The method for producing 1,1,2,2-tetrafluoro-1-(2,2,2-trifluoroethoxy)ethane according to claim 4, wherein when TFEO and TFE are continuously supplied into the reactor, the supplying molar ratio (TFE/TFEO) of TFE to TFEO is at least 1.

6. The method for producing a fluoroalkyl ether according to claim 1, wherein an aprotic polar solvent is used as the solvent.

7. The method for producing a fluoroalkyl ether according to claim 1, wherein an alkali metal alkoxide or an alkali metal hydroxide is used as the catalyst.

8. The method for producing a fluoroalkyl ether according to claim 1, wherein the concentration of the fluoroalkyl alcohol present in the reactor is at most 3 mass % based on the total organic component present in the reactor at the time of distillation after completion of the reaction or at the time of purification after the reaction.

9. The method for producing a fluoroalkyl ether according to claim 1, wherein the concentration of the fluoroalkyl alcohol present in the reactor is at most 1 mass % based on the total organic component present in the reactor at the time of distillation after completion of the reaction or at the time of purification after the reaction.

10. The method for producing a fluoroalkyl ether according to claim 2, wherein in formula 1 a is an integer ranging from 1 to 10.

11. The method for producing a fluoroalkyl ether according to claim 2, wherein in formula 1 a is an integer ranging from 2 to 4.

12. The method for producing a fluoroalkyl ether according to claim 2, wherein in formula 1 e is 0.

13. The method for producing a fluoroalkyl ether according to claim 2, wherein the fluoroalkyl alcohol is selected from the group consisting of CF$_3$CH$_2$OH, CF$_3$CF$_2$CH$_2$OH, CF$_3$(CF$_2$)$_2$CH$_2$OH, CF$_3$(CF$_2$)$_3$CH$_2$OH, CF$_3$(CF$_2$)$_4$CH$_2$OH, CF$_3$(CF$_2$)$_5$CH$_2$OH, CF$_3$(CF$_2$)$_6$CH$_2$OH, CHF$_2$CF$_2$CH$_2$OH, CHF$_2$(CF$_2$)$_3$CH$_2$OH, CHF$_2$(CF$_2$)$_5$CH$_2$OH, CF$_3$CHFCF$_2$CH$_2$OH and CHF$_2$CF(CF$_3$)CH$_2$OH.

14. The method for producing a fluoroalkyl ether according to claim 3, wherein the compound represented by formula 2 is selected from the group consisting of CF$_2$=CF$_2$, CF$_2$=CHF, CF$_2$=CH$_2$ and CF$_2$=CFCF$_3$.

15. The method for producing a fluoroalkyl ether according to claim 1, wherein said fluoroalkyl ether is 1,1,2,3,3,3-hexafluoro-1-(2,2,3,3-tetrafluoropropoxy)propane, said compound of formula 1 is 2,2,3,3-tetrafluoro-1-propanol and said compound of formula 2 is hexafluoropropene.

16. The method for producing a fluoroalkyl ether according to claim 1, wherein said fluoroalkyl ether is 1,1,2,3,3,3-hexafluoro-1-(2,2,2-trifluoroethoxy)propane, said compound of formula 1 is 2,2,2-trifluoroethanol, and said compound of formula 2 is hexafluoropropene.

17. The method for producing a fluoroalkyl ether according to claim 1, wherein said catalyst is at a concentration ranging from 0.005 to 1 mol equivalent to the fluoroalkyl alcohol.

18. The method for producing a fluoroalkyl ether according to claim 6, wherein said aprotic solvent is selected from the group consisting of a straight chain ether, a cyclic ether, and a nitrile compound.

19. The method for producing a fluoroalkyl ether according to claim 6, wherein said aprotic solvent is a glyme.

20. The method for producing a fluoroalkyl ether according to claim 1, wherein the concentration of the solvent in the reactor ranges from 0.01/1 to 0.8/1 by mass ratio to the total amount of the fluoroalkyl ether and the solvent.

* * * * *